United States Patent [19]
Burmer

[11] Patent Number: 6,087,103
[45] Date of Patent: Jul. 11, 2000

[54] TAGGED LIGAND ARRAYS FOR IDENTIFYING TARGET-LIGAND INTERACTIONS

[75] Inventor: Glenna C. Burmer, Seattle, Wash.

[73] Assignee: Lifespan Biosciences, Inc., Seattle, Wash.

[21] Appl. No.: 09/034,622

[22] Filed: Mar. 4, 1998

[51] Int. Cl.[7] .............................. C12Q 1/68; G01N 33/53; C07K 14/00; C07H 21/04
[52] U.S. Cl. ............................... 435/6; 435/7.1; 530/350; 536/23.1
[58] Field of Search .................. 435/6, 7.1; 530/350; 536/23.1

[56] References Cited

U.S. PATENT DOCUMENTS

| | | | |
|---|---|---|---|
| 5,143,854 | 9/1992 | Pirrung et al. | 436/518 |
| 5,412,087 | 5/1995 | McGall et al. | 536/24.3 |
| 5,585,275 | 12/1996 | Hudson et al. | 436/518 |
| 5,591,646 | 1/1997 | Hudson et al. | 436/518 |
| 5,677,195 | 10/1997 | Winkler et al. | 436/518 |

FOREIGN PATENT DOCUMENTS

WO 96/41011  12/1996  WIPO.

OTHER PUBLICATIONS

Hendrickson et al., "High sensitivity multianalyte immunoassay using covalent DNA–labeled antibodies and polymerase chain reaction", *Nucleic Acid Research* 23:3 522–529, (1995).

Thompson et al., "Synthesis and Applications of Small Molecule Libraries", *Chem. Rev.* 96: 555–600, (1996).

*Primary Examiner*—Robert A. Schwartzman
*Attorney, Agent, or Firm*—Townsend and Townsend and Crew

[57] ABSTRACT

The present invention relates generally to high throughput screening methods. More particularly, the present invention provides screening methods that can readily be used to identify simultaneously multiple proteins or compounds that interact with multiple ligands, using a tagged array of ligands.

31 Claims, 1 Drawing Sheet

6,087,103

TAGGED LIGAND ARRAYS FOR IDENTIFYING TARGET-LIGAND INTERACTIONS

CROSS REFERENCE TO RELATED APPLICATIONS

Not applicable.

FEDERALLY SPONSORED RESEARCH OR DEVELOPMENT

Not applicable.

FIELD OF THE INVENTION

The present invention relates generally to the field of high throughput screening methods. More particularly, the present invention relates to screening methods that can readily be used to identify simultaneously multiple proteins or compounds that interact with multiple ligands, using a tagged array of ligands.

BACKGROUND OF THE INVENTION

High throughput screening methods in drug discovery traditionally have involved analyzing thousands of potential ligand compounds against a single target, e.g., a polypeptide, peptide, or a small chemical molecule, using microtiter assay methodology. Recent advances in high density array and microchip technology have reduced the number of these interactions and have increased the number of substances that can be assayed. In addition, the volume of compounds screened using such methods would be greatly increased by simultaneous detection of multiple targets interacting with multiple ligands.

Despite the great value that screening libraries of molecules has for identifying useful pharmaceutical compounds or improving the properties of a lead compound, the difficulties of screening such libraries has limited the impact that these methods should have made in drug discovery and development. Thus, there is a continued need for developing methods of simultaneously screening for multiple target-ligand interactions for drug discovery and the development of lead compounds.

SUMMARY OF THE INVENTION

The present invention thus provides methods of simultaneously screening multiple targets and ligands, which can be used to identify new pharmacological, diagnostic, experimental, or other useful agents. The methods of the present invention employ an array of pooled, tagged ligands, where each ligand is bound to a unique tag that has a known address. The tag address corresponds to the ligand address, allowing identification of the ligand via identification of the tag. In this manner, ligands can be pooled and reacted with many targets at the same time, because the tag provides a means for identifying a specific ligand. In one embodiment, the present invention thus provides high throughput methods for screening multiple target and ligand polypeptides encoded by partial or full cDNA sequences.

In one aspect, the present invention provides a method of screening a target for ligand binding. The method comprises the steps of: a. providing a library of tags, each tag having a known tag address; b. providing a library of ligands, each ligand having a ligand address that corresponds to a tag address; c. binding a tag having a known address to each ligand to create tagged ligands; d. incubating a target with at least two tagged ligands; e. determining whether or not a tagged ligand binds to a target; and f. identifying the tagged ligand by identifying the tag having a known address bound to the tagged ligand, wherein the tag address indicates the corresponding ligand address.

In one preferred embodiment, the tag is an oligonucleotide. In another embodiment, the oligonucleotide is expressed from a library of recombinant plasmids. In another embodiment, each oligonucleotide has the same set of two distinct endonuclease restriction sites. In another embodiment, the method further comprises the steps of amplifying the oligonucleotide and hybridizing the amplified oligonucleotide to a membrane corresponding to the tag address of each oligonucleotide. In another embodiment, each oligonucleotide comprises a label. In another embodiment, the label is selected from the group consisting of biotin, digoxigenin, and a fluorescer.

In one embodiment, the ligand is a protein expressed from a cDNA library. In another embodiment, the target is a protein expressed from a cDNA library. In another embodiment, the target protein and the ligand protein are expressed from a single cDNA library.

In one embodiment, each tag address or ligand address is identified by reference to a matrix. In another embodiment, each tag address or ligand address is provided by a well in a microtiter plate and a corresponding location on a membrane.

In one embodiment, the step of incubating further comprises pooling the tagged ligands prior to incubation with the target.

In one embodiment, the target is bound to a solid support.

In one embodiment, the step of incubating comprises incubating more than one target with the tagged ligands.

In another aspect, the present invention provides a method of simultaneously screening target proteins for ligand binding, the method comprising the steps of: a. providing an library of recombinant oligonucleotides, each oligonucleotide having a known tag address that is located by reference to a matrix; b. providing an expressed cDNA library of ligand proteins, each ligand protein having a ligand address that corresponds to the tag address; c. binding each ligand protein to an oligonucleotide having a known tag address to create tagged ligand proteins; d. pooling the tagged ligand proteins; e. incubating an expressed cDNA library of target proteins with the pooled tagged ligand proteins; f. determining whether or not a tagged ligand protein binds to a target protein; g. amplifying the oligonucleotides; h. hybridizing the amplified oligonucleotides to a membrane corresponding to the tag address of each oligonucleotide; and i. identifying the tagged ligand protein by identifying the oligonucleotide having a known tag address bound to the tagged ligand protein, wherein the tag address indicates the corresponding ligand address.

In another aspect, the present invention provides a method of simultaneously screening for cancer cell autocrine ligands, the method comprising the steps described above.

In another aspect, the present invention provides an array of microtiter plates, comprising: a first plate comprising wells containing a library of tags, wherein each well contains a unique tag, thereby providing each tag with a known address; and second plate comprising wells containing a library of ligands, wherein each ligand is bound to a tag having a known address, and wherein each well contains a unique ligand, thereby providing the ligand with an address corresponding to the oligonucleotide address.

In one embodiment, the array of plates further comprises a third plate comprising wells containing a library of targets, wherein each well contains a unique target that is contacted with tagged ligands pooled from the second plate.

Other features, objects and advantages of the invention and its preferred embodiments will become apparent from the detailed description which follows.

DETAILED DESCRIPTION OF THE INVENTION

I. Introduction

Figure 1:
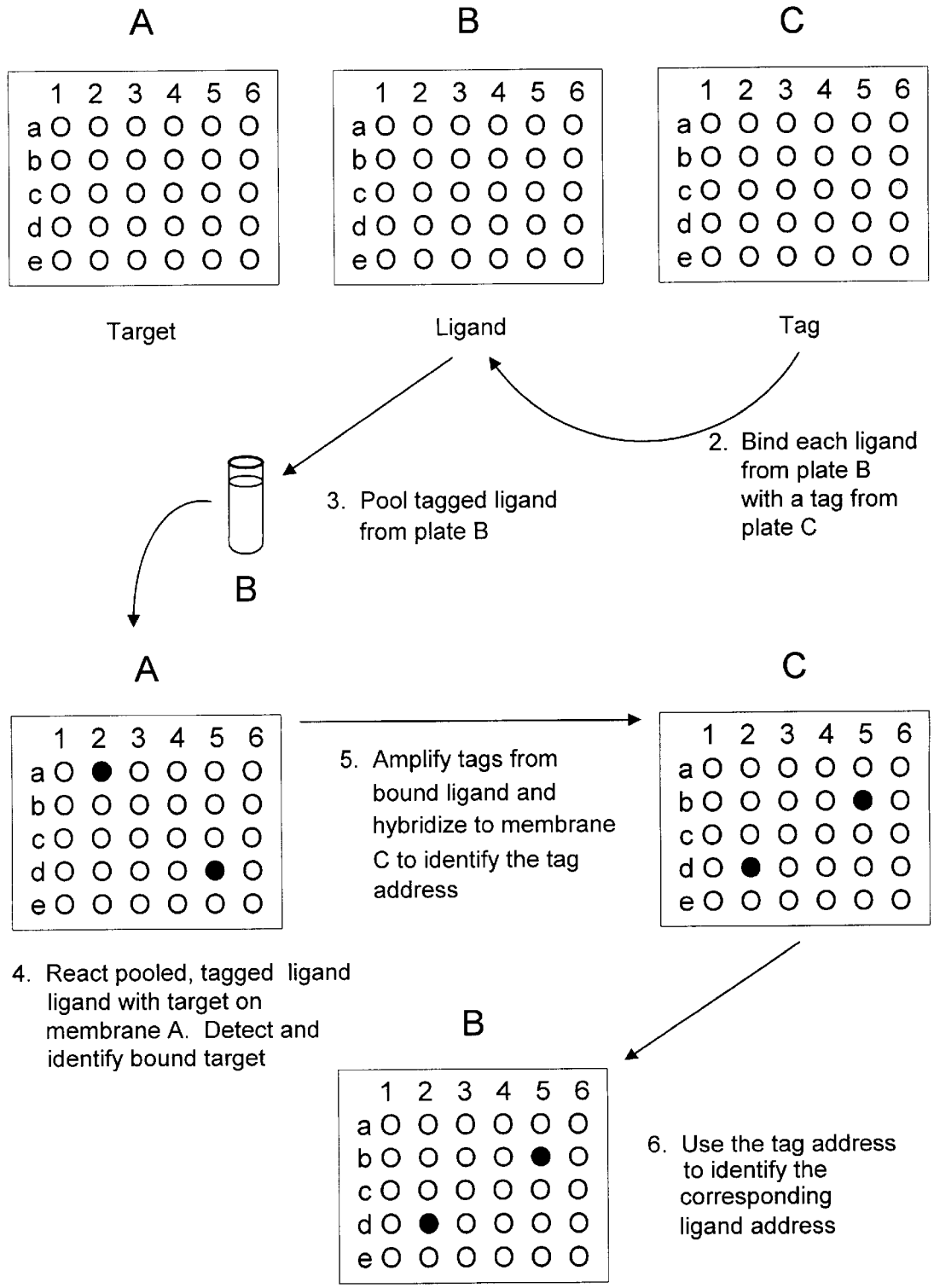
FIG. 1 illustrates on example of the invention and shows an array of plates, where plate A represents the target plate, plate B represents the ligand plate, and plate C represents the tag plate. This figure also schematically represents the steps of (1) providing tagged ligands with an address corresponding to a tag, (2) pooling the tagged ligands and reacting them simultaneously with the targets, (3) identifying bound ligand, (4) amplifying the tag and identifying the tag address, and (5) identifying the corresponding tagged ligand.

The present invention provides methods of screening compound arrays that can be used simultaneously to identify multiple target-ligand interactions, using pooled, tagged ligands where the tag has a known address corresponding to the ligand. As such, the methods and kits of the present invention provide for simple and relatively inexpensive means to determine, e.g., protein-protein or protein-ligand interactions. These screening methods have a variety of uses, including drug discovery of compounds, e.g., small organic molecules, peptides, and polypeptides that bind to target proteins, identification of mutant proteins that have enhanced or inhibited binding, identification of DNA binding proteins, identification of cancer autocrine pathways, diagnostic, and experimental uses. The methods of the invention are particularly advantageous for simultaneous, high throughput screening of multiple polypeptide ligands and targets that are encoded by partial or full cDNAs and genes. Basically, the methods provide for:

A. Providing Libraries of Tags, Ligands, and Targets

Libraries of tags, ligands, and targets are provided and each library is arrayed spatially, for example, in a matrix such as a microtiter dish, so that each well of the dish has a single library member. The arrays are typically duplicated onto membranes. In a preferred embodiment, the tags are oligonucleotides cloned into vectors. In another preferred embodiment, the ligands and targets are proteins expressed from cDNA libraries.

B. Binding Tags to Ligands to Provide Tagged Ligands

Each ligand is bound to a tag in a manner so that the tags and ligands correspond to one another, providing an address for the ligand that corresponds to the tag address, e.g., spatially, where a tag from well C1 is bound to a ligand from well B1, etc. The tag or the ligand also contains one or more detectable moieties, for determining whether the ligand has bound to the target. In one preferred embodiment, the tags are amplified from plate C using known primers, and then bound to the ligand using a coupling reagent. In another preferred embodiment, the primers incorporate biotin molecules at the 3' end of the amplified oligonucleotide (a label), and a primary amine group at the 5' end of the amplified oligonucleotide (a means for coupling the oligonucleotide to the ligand).

C. Determining Ligand-target Interactions

Once the ligands are tagged, the tagged ligands are pooled and incubated with the targets. The reaction is washed and then ligand-target binding is determined by identifying a detectable moiety associated with the ligand or its tag, which is now also associated with a target.

D. Identifying the Tagged Ligand

Each tagged ligand is identified by first matching the tag to its address on its point of reference, e.g., plate C, and then decoding the corresponding address of the ligand on its point of reference, plate B. Thus, the identity of the ligand interacting with a particular target is revealed via the address of the tag. In a preferred embodiment, the address of the tag is determined by amplifying an oligonucleotide tag and hybridizing it to the membrane duplicate of plate C, thereby demonstrating the source of the tag.

Each of the foregoing steps will be described in greater detail hereinbelow.

II. Definitions

As used herein, the following terms have the meanings ascribed to them unless specified otherwise.

The term "tag" refers to a molecule with a recognizable feature that allows it to be distinguished from other tag molecules, e.g., a distinguishable nucleotide or amino acid sequence, shape, size, mass, color, optical density, differential absorbance or emission of light, chemical reactivity, magnetic or electronic properties and the like. Preferred examples of tags include oligonucleotide tags and fluorescers.

The term "ligand" is a relative term that refers to a molecule that binds to or interacts with a target molecule. Typically the nature of the interaction or binding is non-covalent, e.g., by hydrogen, electrostatic, or van der waals interactions, however, binding may also be covalent. The ligand may be, e.g., a small organic molecule, a peptide, or polypeptide.

The term "target" is a relative term that refers to a molecule that binds to or interacts with a ligand molecule. Typically the nature of the interaction or binding is non-covalent, e.g., by hydrogen, electrostatic, or van der waals interactions, however, binding may also be covalent. The target may be, e.g., a small organic molecule, a peptide, or polypeptide, or a polynucleotide.

The term "address" refers to a reference location of a molecule, typically a spatial location. The address of a molecule can be provided, e.g., by reference to a matrix, or by reference to a well in a microtiter plate, or by reference to a location on a membrane. "Matrix" refers to an array of elements into rows and columns.

"Nucleic acid" refers to deoxyribonucleotides or ribonucleotides and polymers thereof in either single- or double-stranded form. Unless specifically limited, the term encompasses nucleic acids containing known analogues of natural nucleotides, which have similar binding properties as the reference nucleic acid and are metabolized in a manner similar to naturally occurring nucleotides, e.g., phosphorothioates, phosphoramidates, methyl phosphonates, chiral-methyl phosphonates, 2-O-methyl ribonucleotides, peptide-nucleic acids (PNAs), and the like. Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). The term nucleic acid is used interchangeably with gene, cDNA, and mRNA encoded by a gene.

The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

A "label" is a composition detectable by spectroscopic, photochemical, biochemical, immunochemical, or chemical means. For example, useful labels include $^{32}P$, fluorescent dyes, electron-dense reagents, enzymes (e.g., as commonly used in an ELISA), biotin, digoxigenin, or haptens and proteins for which antisera or monoclonal antibodies are available. The label is bound, either covalently or non-covalently, to the tag and/or the ligand, and more than one type of label can be bound to either or both of the tag and ligand. Thus, for example, an oligonucleotide tag can be covalently bound to a biotin group, where the oligonucleotide tag is then bound to a ligand that has a fluorescer attached to the ligand.

As used herein a "nucleic acid probe or oligonucleotide primer" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

A "labeled nucleic acid probe or oligonucleotide" is one that is bound, either covalently, through a linker, or through electrostatic, van der Waals or hydrogen bonds to a label such that the presence of the probe may be detected by detecting the presence of the label bound to the probe.

"Amplification" primers are oligonucleotides comprising either natural or analogue nucleotides that can serve as the basis for the amplification of a select nucleic acid sequence. They include, e.g., polymerase chain reaction primers and ligase chain reaction oligonucleotides.

The term "recombinant" when used with reference, e.g., to a cell, or nucleic acid, or vector, indicates that the cell, or nucleic acid, or vector, has been modified by the introduction of a heterologous nucleic acid or the alteration of a native nucleic acid, or that the cell is derived from a cell so modified. Thus, for example, recombinant cells express genes that are not found within the native (non-recombinant) form of the cell or express native genes that are otherwise abnormally expressed, under expressed or not expressed at all.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

A "plasmid" can be an expression vector, or if it does not contain a promoter sequence operably linked to the recombinant nucleic acid of interest, it can simply be a self-replicating, extrachromasomal element that allows propagation of a cloned nucleic acid in prokarotes and/or eukaryotes.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. A "constitutive" promoter is a promoter that is active under most environmental and developmental conditions. An "inducible" promoter is a promoter that is under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular) DNA or RNA. The phrase "stringent hybridization conditions" refers to conditions under which a probe will hybridize to its target subsequence, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes,* "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents as formamide.

The phrase "a sequence encoding a gene product" refers to a nucleic acid that contains sequence information, e.g., for a structural RNA such as rRNA, a tRNA, the primary amino acid sequence of a specific protein or peptide, a binding site for a trans-acting regulatory agent, an antisense RNA or a ribozyme. This phrase specifically encompasses degenerate codons (i.e., different codons that encode a single amino acid) of the native sequence or sequences which may be introduced to conform with codon preference in a specific host cell.

The phrase "specifically (or selectively) binds" to a compound, peptide, or protein or "specifically (or selectively) reactive with," when referring to a compound, protein, or peptide, refers to a binding reaction that is determinative of the presence of the protein in a heterogeneous population of proteins and other biologics. Thus, for example, under designated immunoassay conditions, the specified antibodies bind to a particular protein at a level at least two times the background and do not substantially bind in a significant amount to other proteins present in the sample. Typically a specific or selective binding reaction will be at least twice background signal or noise and preferably more than 10 to 100 times background.

The terms "substrate" and "solid support" typically denote a material having a rigid or semi-rigid surface, e.g., a membrane, a microtiter dish, etc.

"Synthetic" refers to a compound that is produced by in vitro chemical or enzymatic synthesis, in contrast to compounds that are produced inside a cell, e.g., proteins and nucleic acid libraries that are propagated in living host cells.

III. Providing Tag, Target, and Ligand Libraries

A. General Overview of Tag, Target, and Ligand Libraries

Libraries of tags, ligands, and targets can be composed of a variety of different types of molecules. Typically, the ligands and targets are polypeptides, peptides, and small organic molecules, with polypeptides and proteins a preferred embodiment. The target molecules can also be nucleic acids. Typically, the tags are detectable molecules such as fluorescers and oligonucleotides.

For tag libraries, libraries of oligonucleotides are typically obtained by combinatorial synthesis using standard techniques known to those of skill in the art (see, e.g., U.S. Pat. Nos. 5,677,195 and 5,412,087). Oligonucleotide libraries can also be prepared by synthesizing oligonucleotides or cloning small nucleic acid fragments, and then optionally subcloning the oligonucleotides into an expression vector, as described below. Oligonucleotides can be chemically synthesized, e.g., according to the solid phase phosphoramidite triester method first described by Beaucage & Caruthers, *Tetrahedron Letts.* 22:1859–1862 (1981), using an automated synthesizer, as described in Van Devanter et. al., *Nucleic Acids Res.* 12:6159–6168 (1984). Purification of oligonucleotides can be achieved, e.g, by native acrylamide gel electrophoresis or by anion-exchange HPLC as described in Pearson & Reanier, *J. Chrom.* 255:137–149 (1983). Libraries of fluorescers are obtained by incorporating fluorescent conjugated nucleotides into the oligonucleotides by standard methodology, such as that described in *Molecular Probes, Handbook of Fluorescent Probes and Research Chemicals* (Haugland, ed., 6th ed.).

For target and ligand libraries, libraries of small organic molecules are obtained by combinatorial methods known to those of skill in the art (see, e.g., Thompson & Ellman, *Chem. Rev.* 96:555–600 (1996)). Libraries of peptides can also be obtained using combinatorial synthesis (see, e.g., U.S. Pat. Nos. 5,143,854; 5,677,195; 5,412,087). Libraries of peptides and polypeptides can also be obtained by cloning nucleic acids into expression vector, as described below. Natural product libraries (e.g., microbial fermentation broths) can also be used as ligand libraries. Peptide libraries can be prepared by in vitro chemical synthesis by methods known to those skilled in the art, for example, by using standard solid phase techniques. The standard methods include exclusive solid phase synthesis, partial solid phase synthesis methods, fragment condensation, classical solution synthesis, and recombinant DNA technology (see, e.g., Merrifield, *J. Am. Chem. Soc.* 85:2149 (1963); see also the "tea-bag" method of multiple peptide synthesis (Houghton, *Proc. Nat'l. Acad. Sci. USA* 82:5131–5135 (1985); and the split synthesis method (Furka et al., *Int. I. Peptide Protein Res.* 37:487–493 (1991)).

B. Preparation Nucleic Acid Libraries Encoding Tags, Ligands, and Targets

General recombinant nucleic acid methods

For cloning oligonucleotide libraries, and nucleic acid libraries encoding polypeptides and peptides, this invention uses routine techniques in the field of recombinant genetics. Basic texts disclosing the general methods of use in this invention include Sambrook et al., *Molecular Cloning, A Laboratory Manual* (2nd ed. 1989); Kriegler, Gene Transfer and Expression: *A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

The sequence of the cloned genes and synthetic oligonucleotides can be verified using, e.g., the chain termination method for sequencing double-stranded templates of Wallace et al., *Gene* 16:21–26 (1981).

Methods for isolating nucleic acid

In general, the nucleic acid sequences encoding polypeptide and peptide targets and ligands are cloned from cDNA and genomic DNA libraries or isolated using amplification techniques with oligonucleotide primers, and then subcloned into expression vectors. Similarly, in vitro synthesized oligonucleotide tags can be subcloned into expression vectors.

Sources of nucleic acid suitable for use in the methods of the present invention include, but are not limited to, eukaryotic or prokaryotic, invertebrate or vertebrate, mammalian or non-mammalian and plant or other higher eukaryotic sources.

The methods of the present invention are particularly well-suited for the use of cDNA. To make a cDNA library, mRNA is made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263–269 (1983); Sambrook et al., supra; Ausubel et al., supra).

For a genomic library, the DNA is extracted from the tissue and either mechanically sheared or enzymatically digested to yield fragments of about 12–20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180–182 (1977). Colony hybridization is carried out as generally described in Grunstein et al., *Proc. Natl. Acad. Sci. USA.*, 72:3961–3965 (1975).

An alternative method of target and ligand nucleic acid cloning combines the use of synthetic oligonucleotide primers and amplification of RNA or DNA templates (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences directly from mRNA, from cDNA, from genomic libraries or cDNA libraries. Typically, random oligonucleotides are used as primers. Restriction endonuclease sites can be incorporated into the primers. Genes amplified by the PCR reaction can be purified from agarose gels and cloned into an appropriate vector.

The nucleic acid is typically cloned into intermediate vectors before transformation into prokaryotic or eukaryotic cells for replication and/or expression. These intermediate vectors are typically prokaryote vectors or shuttle vectors.

For cloning oligonucleotide tag libraries, oligonucleotides are obtained as described above. Typically, the oligonucleotides are ligated to a set of adaptor molecules that contain two different restriction endonuclease sites. Thus, the structure of the oligonucleotide is as follows: 5'-ANNNNNNNNNNNNC-3', where N is A, T, U, G, or C or an analog thereof, either synthetic or naturally occurring, A is a first restriction site, and C is a second restriction site, e.g., EcoRI, HindIII, PstI, BamHII, KpnI, BglI, SfiI. In this manner, all of the oligonucleotides in the library would share common 3' and 5' ends. The adapters can be included in the oligonucleotides during synthesis, or added at a later stage via ligation of adapters. The restriction endonuclease sites serve a dual purpose as means for cloning the oligonucleotides into expression vectors, and as primer sites for amplification of the oligonucleotides. The length of the oligonucleotide is not critical and is typically from about 8 to about 50 nucleotides in length, preferably about 12 to about 25 nucleotides in length.

Subcloning and expression of isolated nucleic acid

After obtaining oligonucleotide tags and target/ligand nucleic acids encoding polypeptides and peptides, these nucleic acids are cloned into vectors. Typically, the oligonucleotide tags are cloned into plasmid vectors so that individual tags are separated by this cloning procedure. The target ligand nucleic acids are typically cloned into expression vectors, to generate polypeptides.

To obtain expression of a cloned nucleic acid, the expression vector contains a strong promoter to direct transcription, a transcription/translation terminator, and if the nucleic acid encodes a peptide or polypeptide, a ribosome binding site for translational initiation. Suitable bacterial promoters are well known in the art and described, e.g., in Sambrook et al. and Ausubel et al. Bacterial expression systems are available in, e.g., *E. coli,* Bacillus sp., and Salmonella (Palva et al., *Gene* 22:229–235 (1983); Mosbach et al., *Nature* 302:543–545 (1983). Kits for such expression systems are commercially available. Eukaryotic expression systems for mammalian cells, yeast, and insect cells are well known in the art and are also commercially available.

The promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the target, tag, and ligand encoding nucleic acid in host cells. A typical expression cassette thus contains a promoter operably linked to the nucleic acid sequence and signals required for efficient polyadenylation of the transcript, ribosome binding sites, and translation termination. The nucleic acid sequence may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein Bar virus. Other exemplary eukaryotic vectors include pMSG, pAV009/A$^+$, pMT010/A$^+$, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as using a baculovirus vector in insect cells, with the sequence under the direction of the polyhedrin promoter or other strong baculovirus promoters.

The elements that are typically included in expression vectors also include a replicon that functions in *E. coli,* a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of protein, which are then purified using standard techniques (see, e.g., Colley et al., *J. Biol. Chem.* 264:17619–17622 (1989); *Guide to Protein Purification, in Methods in Enzymology,* vol. 182 (Deutscher ed., 1990)). Transformation of eukaryotic and prokaryotic cells are performed according to standard techniques (see, e.g., Morrison, *J. Bact.,* 132:349–351 (1977); Clark-Curtiss & Curtiss, *Methods in Enzymology,* 101:347–362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing target and ligand protein. After the expression vector is introduced into the cells, the transfected cells are cultured under conditions favoring expression of protein.

IV. Providing an Address

The individual components of the tag, ligand, and target libraries are each provided with an address. Preferably, the address is provided spatially, with reference to a position on a matrix, e.g., a well in a microtiter plate or a position on a nitrocellulose or nylon membrane.

The purpose of the substrate is to use spatial positioning of an array (e.g., of targets) to allow identification of the individual target polypeptides. Any suitable substrate can be used to provide an address. In one example, the address is provided by a well in a microtiter dish, and the addresses are typically duplicated on a substrate such as a nylon membrane. The duplicated address is used for hybridization during the step of identifying which oligonucleotide is bound to the tagged ligand. Furthermore, the duplicated address is used for the binding step, in which tagged ligand is incubated with target that is bound, either covalently or noncovalently, to a substrate such as a membrane.

In another example, the individual target polypeptides and their corresponding nucleic acid sequences (from plate A) are conjugated simultaneously onto individual beads that are placed in the wells of plate A. As above, the ligands of plate B are tagged, e.g., with fluorescent-labeled oligonucleotides from plate C, and pooled. The pooled, tagged ligand is reacted with pooled target (bound to beads). Fluorescent activated cell sorting is used to identify ligands that have bound to target. The bead thus identified with FACS contains: (1) the target protein bound to the ligand protein, (2) a nucleic acid coding for the target and (3) a tag that identifies the ligand that has reacted with the target. The individual target and ligand molecules can be identified by amplifying the gene represented on the bead and the oligonucleotide-tag. These amplified sequences can be sequenced or used as probes to identify the targets and tags on plates A and C. As described above, the tags are used further to identify the ligands of plate B.

The substrate is optionally paper, or a membrane (e.g., nitrocellulose or nylon), a microtiter dish (e.g., PVC, polypropylene, or polystyrene), a test tube (glass or plastic), a dipstick (e.g., glass, PVC, polypropylene, polystyrene, latex, and the like), a microcentrifuge tube, or a glass, silica, plastic, metallic or polymer bead or other substrate as described herein. The tag, ligand, or target optionally may be covalently bound, or noncovalently attached to the substrate through nonspecific bonding, e.g., hydrogen, electrostatic, or van der waals forces. Preferably, the target, for the binding reaction to the substrate, is either covalently or noncovalently bound to the substrate, for ease of washing after the binding reaction with the ligand, e.g., by making a duplicate of target plate A on a nylon membrane.

A wide variety of organic and inorganic polymers, both natural and synthetic may be employed as the material for the substrate. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials that are appropriate depending on the assay include paper, glasses, ceramics, metals, metalloids, semiconductive materials, cements and the like. In addition, substances that form gels, such as proteins (e.g., gelatins), lipopolysaccharides, silicates, agarose and polyacrylamides can be used. Where the solid surface is porous, various pore sizes may be employed depending upon the nature of the system.

V. Tagging and Labeling the Ligands, Assays for Detection of a Label

The ligands are first bound to a tag, which provides a corresponding address for the ligand. In addition, either the ligand or the target is bound to a detectable moiety or label, which provides the means for determining whether the ligand interacts with a target. As described above, the tags are molecules such as fluorescers and oligonucleotides, which can be distinguished from other tags of the same class.

The tag is directly coupled to the ligand, to create tagged ligand. The tags are bound to the ligand according to techniques that are known in the art and suitable for the tag of choice. Functional groups which may be used for linking tag to ligand can include carboxylic acids, aldehydes, amino groups, cyano groups, ethylenic groups, hydroxyl groups, mercapto groups and the like (see, e.g., *Essential Molecular Biology* (Brown, ed. 1993); *In Situ Hybridization Protocols* (Cho, ed. 1994).

In one example, oligonucleotide tags can be attached to polypeptide ligands in the following manner. Oligonucleotides are amplified from the oligonucleotide library using primers that correspond to the A and C nonpalindromic restriction sites. The A primer contains an amino modification and the C primer is biotinylated. The A primer thereby incorporates a primary amino at the 5' end of the oligonucleotide, which will react with the carboxy terminus of the ligand polypeptide using coupling reagents such as EDC (Pierce, Rockford, Ill.) . Furthermore, the C primer incorporates a biotin moiety at the 3' end of the oligonucleotide, which acts as a detectable moiety or label for detection of the interaction between bound ligand and target.

As described above, either the tag or the ligand is further bound to a detectable moiety or label. This detectable moiety or label provides a means of determining when a ligand interacts with a target. The detectable moiety or label is bound to the tag or ligand as described above. The detectable moiety or label can be any material having a detectable physical or chemical property. Thus, a label is any composition detectable by spectroscopic, photochemical, biochemical, immunochemical, electrical, optical or chemical means. Useful labels in the present invention include magnetic beads (e.g., DYNABEADS®), fluorescent dyes (e.g., fluorescein isothiocyanate and its derivatives, Texas red, rhodamine and its derivatives, dansyl, umbelliferone and the like), chemiluminescent moieties (e.g., luciferin and 2,3-dihydrophthalazinediones), radiolabels (e.g., $^3$H, $^{125}$I, $^{35}$S, $^{14}$C, or $^{32}$P), enzymes (e.g., horse radish peroxidase, LacZ, CAT, alkaline phosphatase and others commonly used in an ELISA), colorimetric labels such as colloidal gold or colored glass or plastic beads (e.g., polystyrene, polypropylene, latex, etc.), and biotin and avidin or streptavidin, digoxigenin. A wide variety of labels suitable for labeling and conjugation techniques for labeling nucleic acids, proteins, and other molecules are known and are reported extensively in both the scientific and patent literature, and are generally applicable to the present invention. The choice of label depends on the sensitivity required, ease of conjugation of the compound, stability requirements, available instrumentation and disposal provisions.

The label may be coupled directly or indirectly to the tag or ligand according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies or secondary antibodies.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see U.S. Pat. No. 4,391,904.

Means of detecting labels are well known to those of skill in the art.

Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple calorimetric labels may be detected simply by observing the color associated with the label. Thus, in various dipstick assays, conjugated gold often appears pink, while various conjugated beads appear the color of the bead.

As an alternative, the detectable moiety or label can be ligated directly into the vector that contains the nucleic acid encoding the ligand, and expressed as part of the ligand protein. For example, the β-galactosidase gene, green fluorescent protein, or other proteins that can be used to generate a colorimetric signal are placed at the beginning or the end of the cloned ligand protein. This produces a fusion protein that contains both the ligand and a colorimetric detectable moiety. In this example, the tagged oligonucleotides from plate C are bound to each of the fusion protein of plate B. The tagged ligand proteins are then pooled and reacted with the array of proteins on plate or membrane A. The fusion protein that has reacted with a target protein is then detected with a calorimetric reaction. As described above, the identity of the ligand is determined by the corresponding address of its oligonucleotide tag. Variations of this method include adding as the fusion protein any protein that can be detected by a primary antibody, which is then detected by a calorimetric reaction with a secondary antibody using commercially available kits.

VI. Target-ligand Interactions and Assays for Detection

The tagged ligand and target are assayed for ability to bind to each other. Preferably, the tagged ligands are pooled, and then the pool of tagged ligands is incubated under suitable conditions with target bound to a substrate, e.g., a nylon membrane that is a duplicate of the addresses for the target. Typically, the tagged ligands and targets are incubated under conditions that are similar to those used for antibody/antigen binding (see Harlow & Lane, Antibodies: A Laboratory Manual (1988)). For example, the pooled, tagged ligand is suspended in a buffer that has approximately physiological salt and pH conditions and optionally contains protein to prevent non-specific binding, e.g., 3% BSA (bovine serum albumin) in PBS (phosphate buffered saline) or PBS alone. The tagged ligand and target are incubated for approximately 30 minutes at room temperature. The incubation time and temperature are not critical. The reaction is then washed with buffer (e.g., 3% BSA in PBS, or PBS alone) and then suitable assays are performed to detect a label on the tagged ligand that remains bound to the target after washing. Assays for detection of labels are described above and also in Harlow & Lane, supra.

One of skill in the art will appreciate that it is often desirable to minimize non-specific binding in protein binding assays. Particularly, where the assay involves a protein immobilized on a solid substrate it is desirable to minimize the amount of nonspecific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

VII. Identifying Bound Ligands Using the Tag

Once target and ligand that bind to each other have been identified, the tag is identified so that the corresponding address of the ligand can be decoded. Tags are identified by any suitable means, e.g., by sorting or scanning using fluorescence activation, by sequencing, by hybridization, and by amplification.

In one example, oligonucleotide tags are amplified using the polymerase chain reaction (PCR) or, alternatively, using other amplification techniques known to and used by those of skill in the art and discussed in general hereinbelow. In a presently preferred embodiment, the oligonucleotide tags are separately amplified from each site on plate A that gave a signal, by adding appropriate primers (corresponding, e.g, to nonpalindromic restriction sites A and C) and using PCR, usually employing at least about 10 cycles, and preferably about 20–25 cycles. The number of cycles employed will vary depending upon the initial concentration of the first and second nucleic acid sample fragments being amplified. For a general overview of PCR, see, e.g., *PCR Protocols: A Guide to Methods and Applications* (Innis et al., eds. 1990)), and U.S. Pat. Nos. 4,683,195 and 4,683,202.

Once the oligonucleotide tag has been amplified, it is used as a probe for hybridization to membrane C, which contains colonies of plasmid containing cloned oligonucleotides, or which has amplified tags bound to a duplicate filter that has the same addresses as plate C. Typically, the PCR product is labeled via the A and C primers used for amplification. The primers incorporate detectable moieties and labels described above, e.g., biotin and radioactive labels, to detect hybridization to the corresponding oligonucleotide tag on membrane C.

After the address of the oligonucleotide tag has been determined, the corresponding address of the ligand is known. The ligand and target are further analyzed to determine their chemical composition. For example, if the ligand and target are polypeptides encoded by nucleic acids, the nucleic acids can be sequenced to determine the amino acid sequence of the ligand and target polypeptides.

VIII. Kits

In another aspect, the present invention provides kits for carrying out the methods described herein. Combinations of reagents useful in the methods set out above can be packaged together with instructions for using them in the described methods. In particular, such kits can contain a separate microtiter plate and/or membrane for each library, e.g., the tag library, the ligand library, and the target library. The ligand library and the target library may be provided by the user, or may be part of the kit. Preferably, such kits will also contain instructions for carrying out the screening methods described herein. Further, the kits can also contain reagents for assaying the interaction of the ligand and target, e.g., biotin detection assays. If necessary, the kits can contain reagents for binding tags to ligands. Moreover, the kits can contain a pair of primers that can be used to amplify oligonucleotide tags.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Example 1

Identification of Protein-protein Interactions Using Oligonucleotide Tags

In this example, the interaction of each protein in a cell with every other protein in the cell is identified.

First, a full-length cDNA library is made from the cell line of interest, e.g., a cancer cell line. This library is cloned directionally according to standard methods into an expression vector, for expression of the proteins. Individual colonies are isolated into a 96 or 384 microtiter well (see FIG. 1, plate A—the target plate). The array of colonies in the microtiter plate is duplicated onto nitrocellulose or nylon membrane (membrane A) so that the location on the membrane corresponds to a particular well location on the microtiter plate. This step is repeated to produce plate B, the ligand plate.

Second, a library of oligonucleotide tags is made. Oligonucleotides are synthesized according to standard methodology that have the following structure: 5'-ANNNNNNNNNNNNNC-3', where A and C represent restriction endonuclease sites that are nonpalindromic and different from one another. N is A, G, C, U, or T or a synthetic or naturally occurring analog thereof. A suitable vector, e.g., one that has restriction sites A and C, is digested at the polylinker region with restriction endonucleases recognizing the sequences A and C. The oligonucleotides are ligated into the vectors and the complementary strand is filled in. *E. coli* is then transformed with the oligonucleotide library. As described above, individual colonies are arrayed in a microtiter plate, and a duplicate is made on membrane (FIG. 1, plate C—the tag plate, and membrane C). These wells and corresponding sites on the membrane provide the spatial address for the oligonucleotides. Finally, the oligonucleotides are amplified using primers complementary to sites A and C, using amino-modified A and biotinylated C primers.

Next, the library of ligands is tagged with oligonucleotides. A PCR product corresponding to each well of plate C is bound to the protein expressed in each well of plate B so that the wells of plates B and C correspond, e.g., oligonucleotide from well C1 is bound to protein from well B1, oligonucleotide from well C2 is bound to protein in well B2, etc. The oligonucleotides are bound at the 5' amino modified end to the carboxy terminus of the protein using coupling agents such as EDC from Pierce, which links carboxyl groups to primary amines.

Next, the tagged ligands are reacted with the target proteins corresponding to plate A. Aliquots of tagged ligands from plate B are pooled. The pooled, tagged ligand proteins are reacted with the array of target proteins in membrane A, corresponding to plate A. Membrane A is washed extensively to remove unbound ligand and a biotin detection kit is used to determine which colonies on plate A have bound to ligand proteins. This step also gives a spatial address for the protein of plate A.

Finally, the oligonucleotide tag and the target protein that have bound to the protein of membrane A are identified. The oligonucleotide tags from bound ligands are amplified using PCR and biotinylated A and C primers. The A and C primers are removed from the PCR reaction by digesting with the appropriate restriction endonuclease, and purifying the reaction through a steptavidin column, which removes the biotinylated primers. Each amplified oligonucleotide tags is hybridized to membrane C, corresponding to plate C, to identify the address of the oligonucleotide. Once the address of the oligonucleotide tag is known, the original source of the ligand is decoded by identifying the corresponding address of the ligand. The ligand and target protein are further identified by sequencing the cloned nucleic acid inserts in the appropriate wells of plates A and C. Therefore, by correlating the identity of the plate A protein with the identity of the plate B protein via the oligonucleotide tag, it is possible to simultaneously identify multiple target ligand interactions.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purpose.

What is claimed is:

1. A method of screening a target for ligand binding, the method comprising the steps of:
   a. providing a library of tags, each tag having a known tag address that is located by reference to a matrix;
   b. providing a library of ligands, each ligand having a known ligand address that is located by reference to a matrix;
   c. binding a tag having a known address to each ligand to create tagged ligands, wherein the ligand address corresponds to the tag address;
   d. incubating a target with at least two tagged ligands;
   e. determining whether or not at least one tagged ligand binds to a target; and f. identifying said at least one tagged ligand bound to the target by identifying the tag having a known address bound to said at least one tagged ligand, wherein the tag address indicates the corresponding ligand address.

2. The method of claim 1, wherein the tag is an oligonucleotide or a fluorescent molecule.

3. The method of claim 1, wherein the ligand is a protein expressed from a cDNA library.

4. The method of claim 1, wherein the target is a protein expressed from a cDNA library.

5. The method of claim 1, wherein the target and the ligand are proteins expressed from a single cDNA library.

6. The method of claim 1, wherein each tag address corresponds to a matrix that is provided by a well in a microtiter plate and a corresponding location on a membrane.

7. The method of claim 1, wherein each ligand address corresponds to a matrix that is provided by a well in a microtiter plate and a corresponding location on a membrane.

8. The method of claim 1, wherein the target has an address that corresponds to a matrix that is provided by a well in a microtiter plate and a corresponding location on a membrane.

9. The method of claim 1, wherein the step of incubating further comprising pooling the tagged ligands prior to incubation with the target.

10. The method of claim 1, wherein the target is bound to a solid support.

11. The method of claim 1, wherein the step of incubating comprises incubating more than one target with the tagged ligands.

12. The method of claim 2, wherein the oligonucleotide is expressed from a library of recombinant plasmids.

13. The method of claim 2, wherein identifying the tag in step f comprises amplifying the oligonucleotide and hybridizing the amplified oligonucleotide to an oligonucleotide bound to a membrane, wherein the membrane provides the matrix corresponding to the tag address of each oligonucleotide.

14. The method of claim 2, wherein each oligonucleotide has the same set of two distinct nonpalindromic restriction sites.

15. The method of claim 2, wherein each oligonucleotide comprises a label.

16. The method of claim 15, wherein the label is selected from the group consisting of biotin, digoxigenin, and a fluorescer.

17. A method of simultaneously screening target proteins for ligand binding, the method comprising the steps of:
 a. providing a library of recombinant oligonucleotides, each oligonucleotide having a known tag address that is located by reference to a matrix;
 b. providing an expressed cDNA library of ligand proteins, each ligand protein having a known ligand address that is located by reference to a matrix;
 c. binding each ligand protein to an oligonucleotide having a known tag address to create tagged ligand proteins, wherein the ligand address corresponds to the tag address;
 d. pooling the tagged ligand proteins;
 e. incubating an expressed cDNA library of target proteins with the pooled tagged ligand proteins;
 f. determining whether or not at least one tagged ligand protein binds to a target protein;
 g. amplifying the oligonucleotide from said at least one tagged ligand protein bound to the target;
 h. hybridizing the amplified oligonucleotide to an oligonucleotide bound to a membrane, wherein the membrane provides the matrix corresponding to the tag address of each oligonucleotide; and
 i. identifying said at least one tagged ligand protein bound to the target by identifying the oligonucleotide having a known tag address bound to said at least one tagged ligand protein, wherein the tag address indicates the corresponding ligand address.

18. The method of claim 17, wherein each oligonucleotide has the same set of two distinct nonpalindromic restriction sites.

19. The method of claim 17, wherein each oligonucleotide comprises a label.

20. The method of claim 17, wherein the target protein and the ligand protein are expressed from a single cDNA library.

21. The method of claim 17, wherein each tag address corresponds to a matrix that is provided by a well in a microtiter plate and a corresponding location on a membrane.

22. The method of claim 17, wherein each ligand address corresponds to a matrix that is provided by a well in a microtiter plate and a corresponding location on a membrane.

23. The method of claim 17, wherein the target has an address that corresponds to a matrix that is provided by a well in a microtiter plate and a corresponding location on a membrane.

24. The method of claim 17, wherein the target is bound to a solid support.

25. The method of claim 19, wherein the label is selected from the group consisting of biotin, digoxigenin, and a fluorescer.

26. A method of simultaneously screening for ligands expressed by a cancer cell that bind to targets expressed by a cancer cell, the method comprising the steps of:
 a. providing a library of tags, each tag having a known tag address that is located by reference to a matrix;
 b. providing an expressed cancer cell cDNA library of ligand proteins, each ligand protein having a known ligand address that is located by reference to a matrix;
 c. binding a tag having a known address to each ligand protein to create tagged ligand proteins, wherein the ligand address corresponds to the tag address;
 d. expressing target proteins from the cancer cell cDNA;
 e. incubating the target proteins with the tagged ligand proteins;
 f. determining whether or not a tagged ligand protein binds to a target protein; and
 g. identifying the tagged ligand protein bound to the target by identifying the tag.

27. An array of microtiter plates, comprising:
 a. a first plate comprising wells containing a library of tags, wherein each well contains a unique tag, thereby providing each tag with a known tag address that is located by reference to a matrix;
 b. a second plate comprising wells containing a library of ligands, each ligand having a known ligand address that is located by reference to a matrix, wherein each ligand is bound to a tag having a known address, and wherein each well contains a unique ligand, thereby providing the ligand with an address corresponding to the tag address.

28. The array of plates according to claim 27, further comprising a third plate comprising wells containing a library of targets, wherein each well contains a unique target that is contacted with tagged ligands pooled from the second plate.

29. The array of plates according to claim 27, wherein the tag is an oligonucleotide.

30. An array of microtiter plates, comprising:
   a. a first plate comprising wells containing a library of oligonucleotide tags, wherein each well contains a unique oligonucleotide tag, thereby providing each oligonucleotide tag with a known tag address that is located by reference to a matrix;
   b. a second plate comprising wells containing a library of ligands, each ligand having a known ligand address that is located by reference to a matrix, wherein each ligand is bound to an oligonucleotide tag having a known address, and wherein each well contains a unique ligand, thereby providing the ligand with an address corresponding to the tag address.

31. The array of plates according to claim 30, further comprising a third plate comprising wells containing a library of targets, wherein each well contains a unique target that is contacted with tagged ligands pooled from the second plate.

* * * * *

UNITED STATES PATENT AND TRADEMARK OFFICE
CERTIFICATE OF CORRECTION

PATENT NO. : 6,087,103
DATED : July 11, 2000
INVENTOR(S) : Glenna C. Burmer

It is certified that error appears in the above-identified patent and that said Letters Patent is hereby corrected as shown below:

Claim 26(g),
Please delete the period after the word "tag" and then add the following text:

-- having a known address bound to the tagged ligand, wherein the tag address indicates the corresponding ligand address, thereby identifying a cancer cell ligand that binds to a cancer cell target. --

Claim 28,
Please omit the number "27" and insert the number -- 30 --.

Signed and Sealed this

Fourth Day of December, 2001

Attest:

NICHOLAS P. GODICI
*Attesting Officer*  *Acting Director of the United States Patent and Trademark Office*